(12) United States Patent
Alberici et al.

(10) Patent No.: US 6,214,342 B1
(45) Date of Patent: *Apr. 10, 2001

(54) METHOD FOR INCREASING MEAN SURVIVAL TIMES OF TRANSPLANTS WITH LFA-1-SPECIFIC ANTIBODIES

(75) Inventors: Gilles Alberici, Lyons; Pierre Caudrelier, Dardilly; Brigitte Le Mauff, Nantes; Maryvonne Hourmant, Nantes; Jean-Paul Soulillou, Nantes, all of (FR)

(73) Assignee: Imtix-Sangstat, Lyons (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/491,957

(22) PCT Filed: Jan. 21, 1994

(86) PCT No.: PCT/FR94/00071

§ 371 Date: Oct. 30, 1995

§ 102(e) Date: Oct. 30, 1995

(87) PCT Pub. No.: WO94/16728

PCT Pub. Date: Aug. 4, 1994

(30) Foreign Application Priority Data

Jan. 21, 1993 (FR) .................................................. 93 00584

(51) Int. Cl.$^7$ .......................... A61K 39/395; C07K 16/28
(52) U.S. Cl. .................................... 424/154.1; 424/130.1; 424/143.1; 424/144.1; 424/153.1; 424/173.1; 530/387.1; 530/388.1; 530/388.2; 530/388.22; 530/388.7; 530/388.73; 530/388.75
(58) Field of Search .............................. 424/141.1, 143.1, 424/144.1, 153.1, 154.1, 130.1, 173.1; 530/388.1, 388.7, 388.75, 387.1, 388.22, 388.2, 388.73

(56) References Cited

U.S. PATENT DOCUMENTS 5,209,928 * 5/1993 Mawas et al. .
5,622,700 * 4/1997 Jardieu et al. .
5,762,933 * 6/1998 Mawas et al. .
5,922,847 * 7/1999 Broudy et al. .

OTHER PUBLICATIONS

ATCC Cell Lines and Hybridomas, Eighth Editions, 1994, Hay et al. (Ed.) American Type Culture Collection, Rockville MD; p. 131.*
Maraninchi, et al "Anti LFA 1 Monoclonal Antibody for the Prevention . . . " *Bon Marrow Transplantation*, 1989, 4, 147–150.
Le Mauff, et al "Effect of Anti–LFA1 (CD11a) Monoclonal . . . " *Transplantation*,52 (2):291–296 (1991).
Fischer et al "Reduction of Graft Failure by a Monoclonal Antibody . . . " *Blood,* vol. 77, No. 2, Jan. 15, 1991, 249–256.
Dantal et al "Use of Monoclonal Antibodies in Human Transplantation" *Current Opinion in Immunology,* 1991, 3:740–747.
van Dijken et al "Evidence that Anti–LFA–1 in Vivo Improves . . . " *Transplantation* vol. 49, 882–886, No. 5, May 1990.
Paul "The Efficacy of LFA–1 and VLA–4 Antibody Treatment in Rat . . . " *Transplantation,* 55, 1196–1199 (1993).
Nakukura et al "A Non–Lymphocyte–Depleting Monoclonal Antibody . . . " *Transplantation Proceedings,* vol. 25, No. 1, Feb. 1993, 809–812.
Isobe et al "Specific Acceptance of Cardiac Allograft . . . " *Science,* Feb. 28, 1992, 1125–1127.
Isobe "Specific Tolerance Induction Against Cardiac Allograft . . . " The Third Department of Intenral Medicine, University of Tokyo, Tokyo, Japan. 8th Int'l Congress of Immunology, Budapest, Hungary, Aug. 23–28, 1992, Abstract.
Cosimi et al "In Vivo Effects of Monoclonal Antibody to ICAM–1 . . . " *The Journal of Immunology,* vol. 144, No. 12, Jun. 15, 1990, 4604–4612.
Berlin et al "Monoclonal Antibodies Against Human T Cell Adhesion . . . " *Transplantation,* vol. 53, No. 4, Apr. 1992, 840–849.

* cited by examiner

Primary Examiner—Phillip Gambel
(74) *Attorney, Agent, or Firm*—Larson & Taylor PLC

(57) ABSTRACT

Mean survival times of a functional transplant of solid organs in a patient are increased by administering to the patient an initial dosing of a therapeutically effective amounts of a monoclonal antibody directed against the human LFA-1 molecule in the two hours after grafting and then administering daily dosing during a period of approximately nine days.

12 Claims, No Drawings

METHOD FOR INCREASING MEAN SURVIVAL TIMES OF TRANSPLANTS WITH LFA-1-SPECIFIC ANTIBODIES

This is a U.S. national phase of PCT/FR94/00071, filed Jan. 21, 1994.

The present invention relates to the use of monoclonal antibodies for the preparation of a medicinal product for preventing the rejection of transplants of solid organs, to medicinal products comprising them and to a medical kit for effecting this prevention. Solid organs are understood to mean, in particular, the kidney, heart, lungs, liver and skin, an well as endocrine glands such as pituitary glands, thyroid and pancreas and cell suspensions extracted from these (for example islets of Langerhans), and the like.

The last decade has seen an improvement in the results of organ, in particular, kidney, transplantations, reflected in an improvement in the survival of the patients and of the grafts. Before 1981, the use of azathioprine (AZA) and of prednisone (P) constituted the means of primary prophylactic immunosuppression in relation to renal transplantation, despite a relatively low rate of survival of the graft. The appearance of cyclosporin A (CsA) enabled graft survival to be significantly improved, approximately 90% surviving at one year (in "Annual Report of United Network for Organ Sharing" 1989, UNOS Eds. Richmond—J. M. Ceaka et al., The UNOS scientific renal transplant registry, in "Clinical transplants" 1989: 1–8 UCLA Eds. Los Angeles), with a prolonged survival of the patients (approximately 95% in a one-year period), but with not-insignificant problems of toxicity an a counterpart. Polyclonal and monoclonal antilymphocyte antibodies have also been included in protocols of prophylaxis and curative treatment of rejection.

It has been possible to show low rates of early graft rejection by a two-stage treatment comprising initially the use of polyclonal antilymphocyte antibodies and than of CsA as principal maintenance immunosuppressant (A. J. Richardson at al., Transplant Internat 1990; 3: 26–31—B. G. Sommer et al., Transplantation 1987; 43: 85–90).

The introduction of monoclonal antibodies (mAb) having defined Specificity has made it possible to envisage a more precise action in term of induction of immunosuppression and treatment of rejection episodes. At the present time, only the antibody OKT3 (anti-CD3 mAb) has received a marketing authorization for the curative treatment of renal transplant rejection episodes (Ortho-clone OKT®3, Product Information, Physicians' Desk Reference, 43rd edition (Medical Economics Company Inc., N. J. Oradell, 1989, pages 1500–1501). However, only limited evidence of its efficacy in preventing kidney transplant rejection (in combination with a chemical immunosuppression) is available. For the moment, no monoclonal antibody has been recognized for this indication.

The LFA-1 molecule (lymphocyte function-related molecule) in an integrin which belongs to the lymphocyte adhesion complex involved in the phenomena of cellular adhesion and intercellular communication and which enhances, in particular, interactions between helper lymphocytes and their target cells. This family of products includes the Mac-1, LFA-1 and Gp150,95 molecules which possess a common beta chain of 95 kD and differ from one another in their alpha chain. The LFA-1 or CD11a/CD18 protein is a dimer of 180 kD present at the surface of bone marrow cells (leucocytic lines), T lymphocytes, NK cells, polymorphonuclear leucocytes and macrophages/monocytes. In vitro, monoclonal antibodies directed against LFA-1 inhibit most of the activities of T cells.

Anti-LFA-1 antibody has been used in children for the transplantation of HLA-incompatible bone marrow (A. Fischer et al., Lancet 1986; ii, (8515): 1058–1061—N. Perez et al., Bone Marrow Transplant 1989; 4: 379–384). Anti-LFA-1 antibodies have also been used in adult leukaemia patients for preventing an HLA-induced T cell-depleted bone marrow transplant rejection (D. Maraninchi et al., Bone Marrow Transplant 1989; 4: 147–150). They have also been used to treat 10 patients displaying an acute graft-versus-host reaction resistant to steroid treatments (A. M. Stoppa et al., Transplant Int. 1991; 4: 3–7).

In relation to renal transplantation, anti-LFA-1 monoclonal antibodies have been used in seven patients for treating episodes of acute transplant rejection (B. Le Mauff et al., Transplantation 1991; 52 (2); 291–296). The antibody used was the monoclonal antibody designated 25.3. Tolerance was good in the six patients who received more than one administration of this antibody. Infections were reported in two patients. However, only one patient, probably the one who experienced the weakest episode of rejection, regained his renal function before rejection, and a back-up treatment had to be instituted in five of them. In conclusion, this antibody was considered to be ineffective for treating the acute rejection occurring in the course of kidney transplantation. Use in the prevention of rejection has not been studied.

P. J. Berlin et al., Transplantation, Vol. 53, No. 4, 1992, Baltimore Md., USA, have described some degree of efficacy of the administration of anti-LFA-1 antibody for blocking the activity of T cells during the rejection of a cutaneous allograft in monkeys, and a slight prolongation of the survival of the graft before rejection. The only graft surviving at three months corresponds to a treatment combining an anti-CD11 and an anti-CD2.

Monoclonal antibodies directed against ICAM-1, the natural ligand for LFA-1, have shown some results in kidney transplant rejection in primates (B. A. Cosimi et al., Leukocyte Adhesion Molecules 1989: 274). The authors suggest that a treatment combining anti-ICAM-1 and anti-LFA-1 antibodies might be more effective (B. S. Cosimi et al., J. of Immunol., 1990, vol. 144, No. 12, 4604–4612).

M. Isobe, Proceedings of Int. Congress of Immunol. Budapest, Aug. 23–28, 1992 (Ed. Hungarian Soc. for Immunol.) Springer, Berlin, 1992, 554, W-90-19, also suggests a synergistic effect of anti-ICAM-1 and anti-LFA-1 monoclonal antibodies in allograft tolerance in rodents.

The prior art, while recognizing some useful properties in anti-LFA-1 antibodies, does not therefore suggest the use of these antibodies for preventing the rejection of transplants of solid organs, except in the form of combinations with other antibodies also involved in cellular adhesion phenomena.

The Applicant has now found that it was possible to prevent the rejection of transplants of solid organs, such as the kidney, by the administration of monoclonal antibody directed against the human LFA-1 (CD11a/CD18) molecule, this being achieved without combination with other antibodies or with cyclosporin A.

He also found that the efficacy of this use was greatly dependent on the implementation of a novel administration protocol.

The subject of the present invention is hence the use of monoclonal antibodies directed against the human LFA-1 molecule for the preparation of a medicinal product intended for the primary treatment for preventing the rejection of transplants of solid organs, in particular the kidney, in man. The monoclonal antibodies are preferably directed against the alpha chain of the LFA-1 molecule.

For the purposes of the present invention, antibodies are understood to mean human antibodies, non-human, for example murine, humanized, chimeric recombinant antibodies or other antibodies, as well as antibody derivatives, fragments and the like. All these antibodies, including the derivatives, may be prepared by standard methods.

The monoclonal antibodies which are useful in the invention may be characterized in that they react with:

T and B lymphocytes, monocytes, macrophages and polymorphonuclear leucocytes;

approximately 60% of thymocytes and prothymocytes;

T cell lines (for example MOLT-4, HPB-ALL and CEM lines);

the KG1 line, isolated from an acute myeloid leukaemia.

The monoclonal antibodies according to the invention have it as their objective to block the LFA-1 molecule and thus to reduce intercellular interactions. The monoclonal antibody should inhibit adhesion and the effector functions of T cells and NK cells.

Apart from the properties of binding, defined above, with the different cell classes, the monoclonal antibodies according to the invention advantageously have all or part of the following properties in vitro:

inhibition of the mixed lymphocyte reaction and, partially, of phytohaemagglutinin (PHA)-induced proliferation;

inhibition of T-dependent cytotoxicity and of NK cytotoxicity;

impairment of the power of adhesion of polymorphonuclear leucocytes to glass;

absence of reaction with the membrane of leucocytes of children suffering from a congenital immunodeficiency of the LFA-1 CR3 receptor and Gp 150,95 complex;

inhibition of the binding of complement component C3bi to its CR3 receptor;

inhibition of the antibody-producing activity of antigen-specific T-helper cells;

partial inhibition of antigen-induced T cell proliferation;

absence of cellular proliferation and of TNF-α production;

decrease (at high concentration) of the proliferative responses induced by the mitogens PMA, ConA, PWM and OKT3 in solution;

decrease in blast cells and in expression of the a chain of the IL-2 receptor (CD25);

decrease in the proliferative responses of SEB-stimulated, monocyte-depleted cell suspensions or of mitomycin-treated alloreactive B cells (MLR).

Preferably, the monoclonal antibody will be a mouse IgG$_1$, and in particular antibody 25.3 (internal reference 25.3.1.19.3B7), also designated 25.3.1 in Leucocyte Typing III, Oxford Sep. 21–26, 1986, deposited with the ECACC collection, PHLS Centre for Applied Microbiology & Research, Porton Down, Salisbury, Wilts, SP4 GJ6, U.K. under reference 92 120 309 on Dec. 3rd, 1992.

The monoclonal antibody intended for preventing the rejection of transplants of solid organs in a recipient is preferably administered at the rate of approximately 1 to 50 mg/day, and in particular approximately 15 to 20 mg/day; preferably over a period ranging from 1 to 30 d., and in particular from 3 to 14; preferably by perfusion, in particular of the order of 30 min.

The subject of the invention is also a medicinal product comprising an active principle at least one monoclonal antibody directed against the human LFA-1 molecule, in isotonic solution at a concentration of approximately 1 mg/ml in a suitable vehicle.

The subject of the invention is also a medicinal product comprising as active principle at least one monoclonal antibody directed against the human LFA-1 molecule, in isotonic aqueous solution for perfusion, and stabilizing agents such as tris(hydroxymethyl)aminomethane and TWEEN 80.

Preferably, for a solution of one liter, the medicinal product in solution comprises from 0.1 to 10 g, and in particular approximately 1 g, of monoclonal antibody, and from 0.1 to 10 g, and in particular approximately 2.4 g, of tris(hydroxymethyl)aminomethane or the like, and from 0.1 to 10 of TWEEN 80, and in particular 2, per ten thousand, in an isotonic solution.

The medicinal products according to the invention preferably comprise a monoclonal antibody directed against the alpha chain of the LFA-1 molecule, and more especially a monoclonal antibody as defined above.

The subject of the invention is also a kit intended for simultaneous or separate administration or administration set over a period of time for the purpose of preventing rejection of transplants of solid organs, comprising:

a medicinal product in which the active principle in at least one antibody directed against the LFA-1 molecule, preferably a monoclonal antibody of the type described above, and at least one other compound which is active in regard to preventing organ transplant rejection, chosen in particular from the following compounds:

tacrolimus (FK-506), azathioprine, a steroid, such as prednisone or an equivalent corticosteroid, cyclosporin A.

The subject of the invention is also a method for preventing the rejection of transplants of solid organs such as the kidney, in which at least one anti-LFA-1 monoclonal antibody as described above and, where appropriate, at least one other agent chosen from those in the above kit is/are administered. Preferably, the monoclonal antibody is administered at the rate of 1 to 50 mg/day, in particular approximately 20 mg/day; preferably by perfusion, in particular of the order of 30 min.

More especially, the subject of the invention is a method for preventing the rejection of transplants of solid organs such as the kidney, characterized in that an initial dose of an anti-LFA-1 antibody is administered shortly, in particular in the two hours, for example one hour, before re-establishment of the vascular continuity of the implanted graft, and daily doses are then administered for approximately 9 days.

The initial dose is preferably 30 mg (2×15 mg), and the following doses, in adults, are advantageously of the order of 15 mg, preferably administered by perfusion into a peripheral vein.

The dosage, expressed with reference to weight, is larger in children.

The method of prevention is noteworthy in that it can be advantageously implemented without any other major medication, in particular without other monoclonal antibodies or anti-T gamma globulins, and without cyclosporin.

Advantageously, cyclosporin treatment may be instituted on the 9th or 10th day at the time anti-LFA-1 treatment is stopped.

The method according to the invention can, moreover, be combined with customary corticoid and azothioprine treatment.

The invention will now be described in greater detail by means of an embodiment of the invention.

Monoclonal antibody 25.3 is harvested after culture in fermenters in a protein-free medium. The weekly supernatants are concentrated and then purified by three chromatographic steps on Q SEPHAROSE FF, then S SEPHAROSE FF, then Q Sepharose FF.

Bottles of 5 ml of antibody 25.3 at a concentration of 1 mg/ml are prepared:

| antibody | 5 mg |
|---|---|
| tris(hydroxymethyl)aminomethane | 12.1 mg |
| NaCl | 43.5 mg |
| TWEEN 80 | 1 mg |
| water for injections   qs | 5 ml |

Immunosuppressant treatments may be combined;

Cyclosporin A (SANDIMMUN®): at the rate of 8 to 10 mg/kg/day administered orally from the 9th day after transplantation; in one to two administrations daily for an indeterminate period; or intravenously at the rate of 2 to 4 mg/kg/day.

Azathioprine (IMUREL®) at the rate of 2 mg/kg/d from the day of transplantation, administered orally or intravenously, for a total dose of 25 mg; administration in a single portion; the daily dose can range from 2 to 2.5 mg/kg.

Steroids: at the rate of 1 mg/kg/d of prednisone or an equivalent corticosteroid, on days 1 to 5, administered orally; from the 6th day, the dose is decreased every 5 days by 10 mg, then complete withdrawal on the 45th day.

Various treatments may be combined if necessary; for example:

oral antifungal such as amphotericin B (FUNGIZONE®) at the rate of 1.5 mg/day for one month, antibiotic such an sulphamethoxazole/trimethoprim (BACTRIM®) at the rate of 800 mg/day for 3 months, treatment for fever: for example paracetamol administered orally at the rate of 650 mg, as required, treatment for pruritus using an antihistamine such as diphenhydramine at the rate of 50 mg administered orally, as required.

Clinical Experience in Prophylaxis of Kidney Transplant Rejection

A non-randomized, open, single-centre phase II clinical trial is carried out using fifteen patients who are to undergo a 1st renal transplantation.

The first patient was included on May 25, 1992. All the patients were monitored for three months post-transplantation.

The first five patients (patients 1 to 5) received 20 mg/day of anti-LFA-1 antibody 25.3 for 10 days. In the light of the clinical and biological results obtained in this first group, the next five patients (patients 6 to 10) received 15 mg/day. The last five patients received 10 mg/day (patients 11 to 15).

Inclusion Criteria

First transplantation of kidney from cadaver, recipient between 18 and 60 years of age, donor between 10 and 60 years of age, duration of cold ischaemia <48 h and obtaining of a signed consent to participate.

Treatment Protocol Used

The antibody is perfused intravenously over a period of 30 minutes from days D1 (day of transplantation) to D10.

Relative to the standard triple therapy protocol customarily used in the centre, the introduction of cyclosporin is delayed to the 9th day post-transplantation in order to achieve the recommended residual levels on withdrawal of anti-LFA-1 (on D10). Azathioprine in administered at a dose of 2 mg/kg/day from D1 to 5, then reduced by 10 mg every 5 days from D6 and withdrawn on D45 post-transplantation.

Tolerance to Injections

The immediate tolerance to the injections is excellent: all the patients received the whole of the treatment. No difference was observed between the groups (20 or 15 mg) in terms of tolerance to the anti-LFA-1 injection.

Biological tolerance: half of the patients became immunized against the antibody, but the immunization always occurred after the last day of treatment (between D12 and D30).

| Clinical course - Summary table | | | | |
|---|---|---|---|---|
| Number of patients | | 5 | 5 | 5 |
| Number of patients who could be evaluated | | 5 | 5 | 4* |
| Anti-LFA-1 (mg/day) for 10 days | | 20 | 15 | 10 |
| Mean monitoring period (days) | | 90 | 90 | 90 |
| Withdrawal of treatment | | 0 | 0 | 0 |
| Immunization | on D15 | 3/5 | 0/5 | 2/4 |
|  | on D30 | 3/5 | 2/5 | 1/4 |
| Rejection episodes | Before D10 | 0 | 0 | 0 |
|  | from D10 to D30 | 0 | 0 | 0 |
|  | from D30 to D90 | 1 | 3 | 2 |
|  | (patient No.) | (1) | (2) | (2) |
| Infectious episodes | | 0 | 3 (2 CMV$_2$ 1 candidiasis) | 4 (2 CMV 1 candidiasis 1 pyelonephritis) |
| Blood creatinine (micromol/l) | | | | |
| mean ± s.e.m (n = 5) | D1 | 545 ± 221 | 516 ± 137 | 617 ± 135 |
|  | D30 | 148 ± 20 | 229 ± 109 | 140 ± 38 |
|  | D90 | 167 ± 48 | 186 ± 118 | 133 ± 22 |

*1 case of immediate arterial thrombosis

All the patients are alive and have a functional transplant at 3 months post-transplantation, with the exception of 1 patient in group 3 who lost his graft through an immediate arterial thrombosis unrelated to a rejection phenomenon.

No rejection episode under anti-LFA-1 treatment was observed. Six patients displayed at least one rejection episode (between the first and the second month). These rejection episodes were all resolved by conventional treatments.

The biological monitoring of the study entailed the study of several parameters.

Measurement of circulating antibody levels was accomplished by an immunoenzymatic test detecting mouse immunoglobulins (Ig) in the serum by reference to a calibration curve of purified 25.3. Both 20 and 15 mg groups display high levels of circulating 25.3, reaching on average 12 and 10 μg/ml at the end of the treatment. The difference between the first and second groups is not statistically significant, and 25.3 is still detectable in both groups on D14, or even D20 in the case of some patients. In the third group, the levels were markedly lower and scattered, but nevertheless significant four days after the last injection.

The antibody does not bring about any major modification of the number of circulating cells; hence it does not have a depleting effect. On the other hand, the circulating cells, and especially lymphocytes and monocytes, are coated with 25.3 to the point of saturation. In effect, when the patients' cells are studied by cytofluorometry, the labelling obtained with a fluorescein-coupled anti-mouse antibody is of the same intensity with or without prior labelling in vitro with a saturating amount of 25.3 (20 μg/mg). This saturation in still observed at D14 in the case of 3/5 of the patients in group I and in the case of all the patients in group II.

The presence of the circulating antibody and saturation of the cells is accompanied by a functional blocking of the cells demonstrated in respect of the adhesion capacities of the T lymphocytes. LFA-1/ICAM-1 molecules are known to be involved in the heterotypic adhesion of T lymphocytes to B lymphoblastoid target cells.

A test of adhesion between the T lymphocytes of the circulating blood and a B line (Daudi) was hence developed. The lymphocytes are isolated on a Ficoll gradient and then labelled with an anti-CD3 coupled to phycoerythrin (7 μg/ml), and the B line is labelled by indirect immunofluorescence with an anti-Daudi monoclonal antibody and then a fluorescein-coupled anti-mouse antibody. The cells, taken up in RPMI medium, are brought into contact in a 1:1 (mononuclear/Daudi cells) ratio, and incubated either at 4° C. or at 37° C. (with and without addition of 25.3, 15 μg/ml). The reaction in stopped by adding 2 volumes of cold medium, and the cells are stored at 4° C. until analysed by cytometry within the 2 h which follow. In the analysis, those CD3+ cells which are doubly positive are measured. These doubly positive events correspond to T-Daudi conjugates, as confirmed by the apparent increase in size (×2 or ×3) of the "doubly" labelled CD3+ cells. The number of conjugates corresponds to the percentage of conjugates obtained at 37° C. minus the percentage obtained in the presence of 25.3 at a concentration of 15 μg/ml.

The results obtained with the patients' cells are expressed in the form of an adhesion index, that is to say expressed with reference to the values obtained in the same experiment with cells of control subjects (healthy donors so an to normalize inter-trial variations).

In all the groups of patients, the adhesion index is at rock-bottom level during the treatment, and then rises gradually between D20 and D30. A single patient, in group I, has recovered a normal adhesion at D15 and displays, moreover, considerable immunization against 25.3, with the presence of anti-idiotype antibodies. The recovery of the adhesion capacities taken place, in fact, at the same time as the desaturation of the circulating cells.

The expression of the LFA-1 molecule on the patients' lymphocytes was also analyzed, during the treatment, by cytofluorometry. A decrease in the intensity of fluorescence of CD11a visualized with 25.3, capable of reaching 50%, could be observed in both groups. This modulation begins as early as the first injection, but is greater between D10 and D15. It is accompanied by an altogether parallel decrease in the expression of CD18, that is to say of the β chain of the LFA-1 molecule.

Seven of the fourteen patients monitored displayed an immunization, without effects during the treatment. Only four patients showed, after the treatment, mouse IgG antibodies that were detectable beyond a dilution to 1/300.

In short, 25.3 is an antibody lacking a depleting effect which, at the doses used, saturates the LFA-1 sites present on the circulating cells and thus brings about a blocking of LFA-1-dependent lymphocyte adhesion capacities. The treatment may be accompanied by a modulation of the cellular expression of the LFA-1 molecule. It in capable of inducing an antibody response which is often small but sometimes (1 case/10 in this study) large, after the treatment period, with the presence of anti-idiotype antibodies.

What is claimed is:

1. A method for increasing mean survival times of a functional transplant of solid organs in a patient, comprising administering to the patient an initial dosing of a therapeutically effective amount of a monoclonal antibody directed against the human LFA-1 molecule in the two hours after grafting, and then administering daily dosing during a period of approximately 9 days.

2. A method according to claim 1, wherein said grafted solid organ is kidney.

3. A method according to claim 1, wherein the monoclonal antibody is directed against the alpha chain of the LFA-1 molecule.

4. A method according to claims 1 or 3, wherein the monoclonal antibody reacts with:

T and B lymphocytes, monocytes, macrophages and polymorphonuclear leucocytes;

approximately 60% of the thymocytes and prothymocytes;

T cell lines;

the line KG1.

5. A method according to claim 1, wherein the monoclonal antibody is a mouse $IgG_1$.

6. A method according to claim 5, wherein the monocolonal antibody is the antibody 25.3 deposited with the ECACC collection under reference 92 120 309.

7. A method according to claim 1, wherein the monoclonal antibody is administered at the rate of approximately 1 to 50 mg of antibody/day.

8. A method according to claim 1, wherein the monoclonal antibody is administered at the rate of approximately 20 mg of antibody/day.

9. A method according to claim 1, wherein the monoclonal antibody is administered by perfusion.

10. A method according to claim 1, wherein the monoclonal antibody is administered by perfusion of approximately 30 minutes.

11. A method according to claim 1, wherein the monoclonal antibody is administered at a loading dose before the revascularization of the graft, and a daily dose is then administered up to the $10^{th}$ day.

12. A method according to claim 1, wherein the monocolonal antibody is administered at a loading dose of 30 mg before the revascularization of the graft, and a daily dose of 15 mg is then administered up to the 10th day.

* * * * *